United States Patent [19]

Burgin

[11] 4,156,424

[45] May 29, 1979

[54] LOCKING ADJUSTABLE SPECULUM

[76] Inventor: Kermit H. Burgin, R.R. #1, Box 334, Whitestown, Ind. 46075

[21] Appl. No.: 901,521

[22] Filed: May 1, 1978

[51] Int. Cl.² .......................... A61B 1/06; A61B 17/02
[52] U.S. Cl. ...................................... 128/18; 128/20; 128/341
[58] Field of Search ..................... 128/341, 345, 3, 17, 128/18, 19, 20, 303 R, 242, 244

[56] References Cited

U.S. PATENT DOCUMENTS

| 605,652 | 6/1898 | Pitt | 128/18 |
|---|---|---|---|
| 1,222,478 | 4/1917 | Sheaff | 128/18 |
| 1,230,873 | 6/1917 | Crossley | 128/20 |
| 1,706,500 | 3/1929 | Smith | 128/20 |
| 1,780,912 | 11/1930 | Gau | 128/3 |
| 3,196,865 | 7/1965 | Rose | 128/20 |

FOREIGN PATENT DOCUMENTS 473451  1/1915  France ...................................... 128/20

Primary Examiner—Stephen C. Pellegrino
Attorney, Agent, or Firm—Jenkins, Coffey & Hyland

[57] ABSTRACT

An adjustable speculum includes a base rotatably supporting a pair of shafts, and a pair of dilating members. Each dilating member has a distal end for contacting and restraining a wall of the orifice and a proximal end for detachably engaging a respective shaft. The base includes a mechanism for adjusting the distance between the shafts whereby the distance between the proximal ends of the dilating members is adjustable. Each shaft includes a portion for preventing the dilating member from rotation with respect to the shaft. The distance between the distal ends of the dilating members is also rotatably adjustable.

13 Claims, 8 Drawing Figures

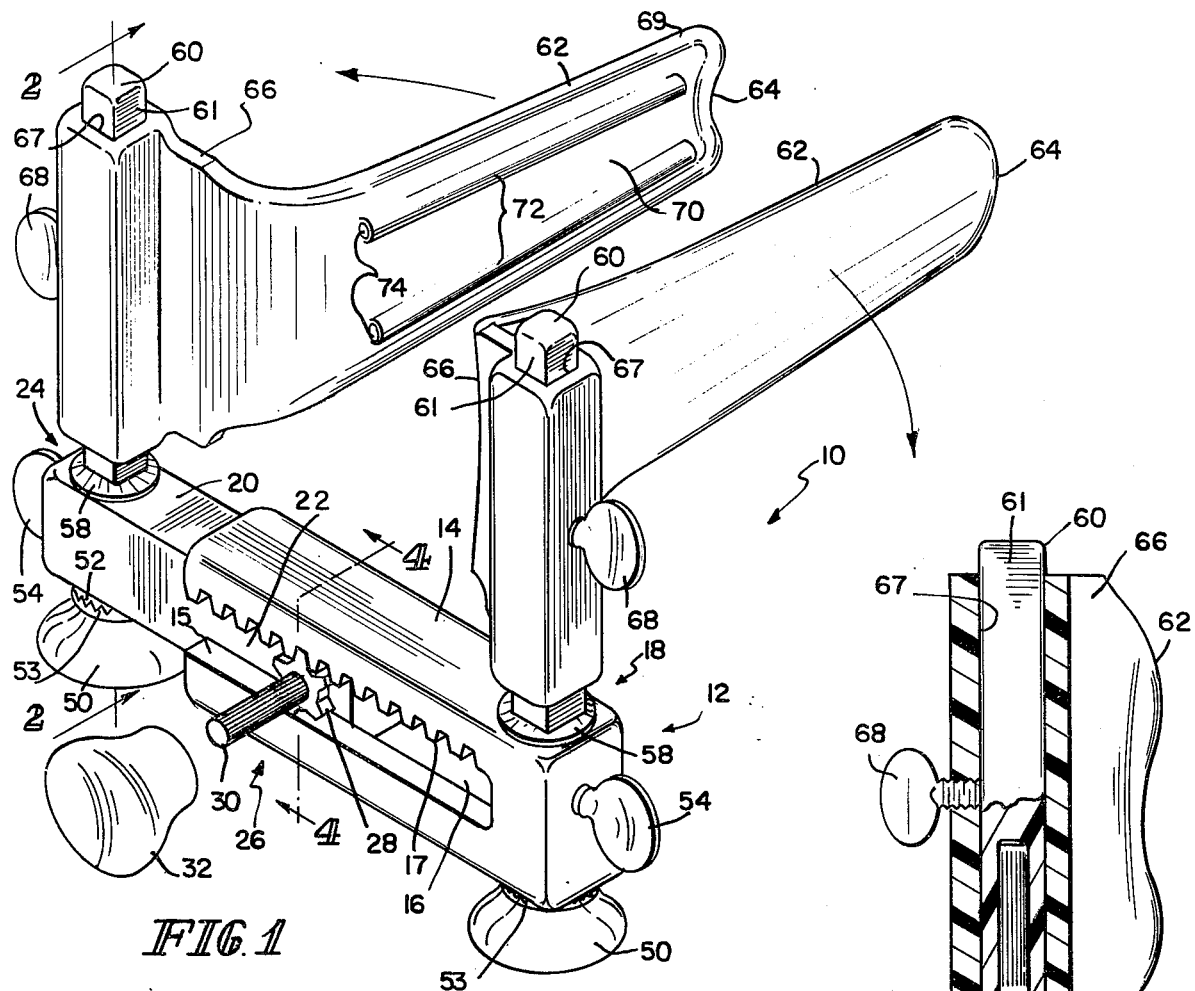
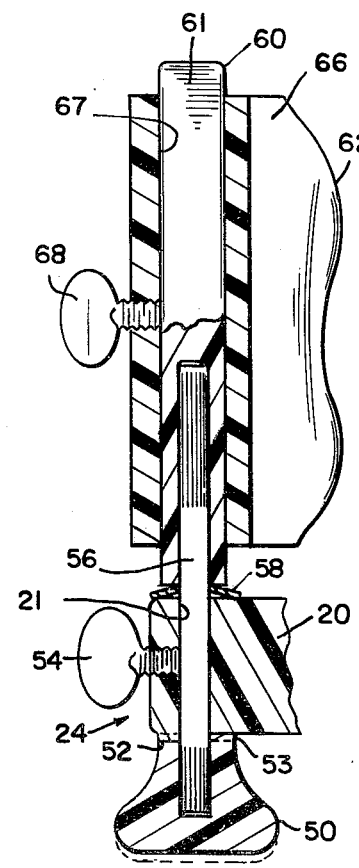
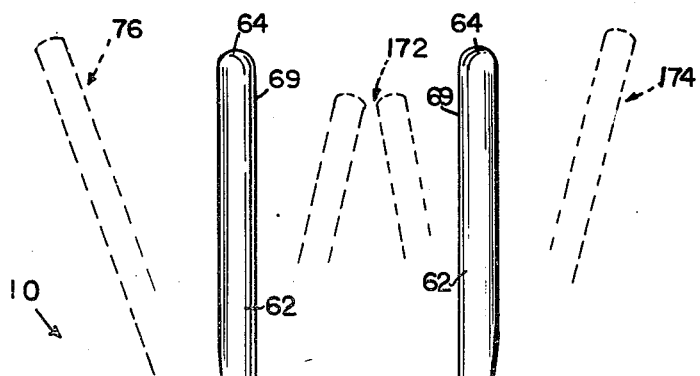
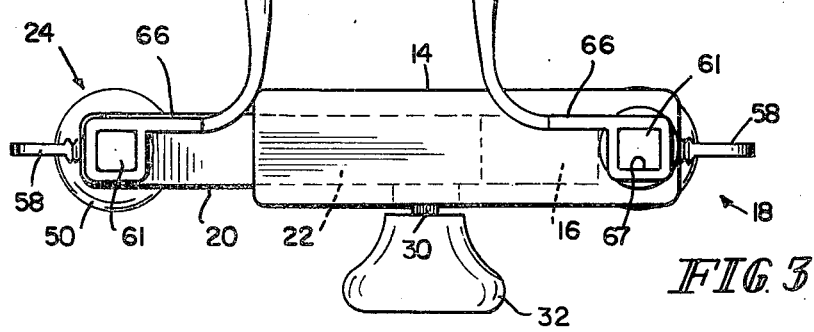

LOCKING ADJUSTABLE SPECULUM

BACKGROUND OF THE INVENTION

1. Field of the Invention

The present invention relates generally to an apparatus for dilating a meatus, orifice or incision and more particularly to a speculum which is self-sustaining and adjustable having means for independently adjusting the distances between the proximal and distal ends of detachable restraining members used to dilate the meatus, orifice or incision and means for independently self-sustaining various desired distances between both the distal and proximal ends thereby leaving the speculum operator's hands free for purposes of examination or other activities.

2. Description of the Prior Art

There are many well-known specula and forceps for enlarging body orifices or incisions for such purposes as examination or surgery. For the most part, however, these well-known devices require sterilization between uses; are not adaptable for use in orifices or incisions having different sizes, shapes, depths and so forth; have at most only one means for adjusting the device to make it adaptable to these variable conditions; and have the means for adjustment situated such that the view and/or the ability of the user to examine the orifice is at least partially obstructed. See for example, the following U.S. patents: Molesworth, U.S. Pat. No. 400,589; Crockett, U.S. Pat. No. 776,302; Joutras, U.S. Pat. No. 1,094,575; and, Radcliff, U.S. Pat. No. 2,217,968. Furthermore, many prior devices require that the user maintain a constant physical force in order to restrain the orifice once it has been enlarged. See for example Pomerene, U.S. Pat. No. 1,170,324.

In a copending application, Ser. No. 811,550, filed June 30, 1977, and entitled "Plastic Forceps," I have disclosed solutions to some of the aforementioned problems associated with prior specula or forceps. It is believed that the improved speculum provided by the present invention provides solutions to all of the problems mentioned hereinabove by providing a high degree of flexibility and various self-sustaining features.

SUMMARY OF THE INVENTION

In accordance with the present invention, an adjustable speculum is provided. The speculum is adaptable for use in enlarging orifices of various sizes, shapes and depths and allows the user thereof substantially unobstructed access to the orifice for purposes of examination and various other functions.

Accordingly, it is a feature of the present invention to provide a speculum which includes a pair of members for restraining and dilating an orifice, each having a distal end for contacting the walls of the orifice and a proximal end for detachably engaging a shaft, and a base supporting the shafts and including means for adjusting the distance between the shafts whereby the distance between the proximal ends of the restraining members is independently adjustable.

It is another feature of the present invention to provide such a speculum wherein the shafts are rotatably coupled to the base and include means fixed to each shaft for preventing the dilating members from rotating on the shafts. The distance between the distal ends of the dilating members is rotatably adjustable independent of adjustments to the proximal ends of the dilating members.

It is another feature of the present invention to provide a speculum including various means for independently sustaining desired distances between both the distal and proximal ends of the dilating members and desired positions of the dilating members along the shafts.

Another feature of the present invention is to provide a speculum having detachable dilating members which may be of various sizes or shapes and which may be either separately sterilized or disposed of after each use.

Other features and advantages of the present invention will be apparent from the following detailed description of an embodiment thereof. The description can best be understood by reference to the accompanying drawings which illustrate the embodiment.

BRIEF DESCRIPTION OF THE DRAWINGS

FIG. 1 is a perspective view of an apparatus constructed in accordance with the present invention;

FIG. 2 is a fragmentary cross-sectional view of the apparatus of FIG. 1 taken generally along section lines 2—2 of FIG. 1;

FIG. 3 is a top plan view of the apparatus of FIG. 1;

DESCRIPTIONS OF ILLUSTRATED EMBODIMENTS

Figures 4, 5, 6:
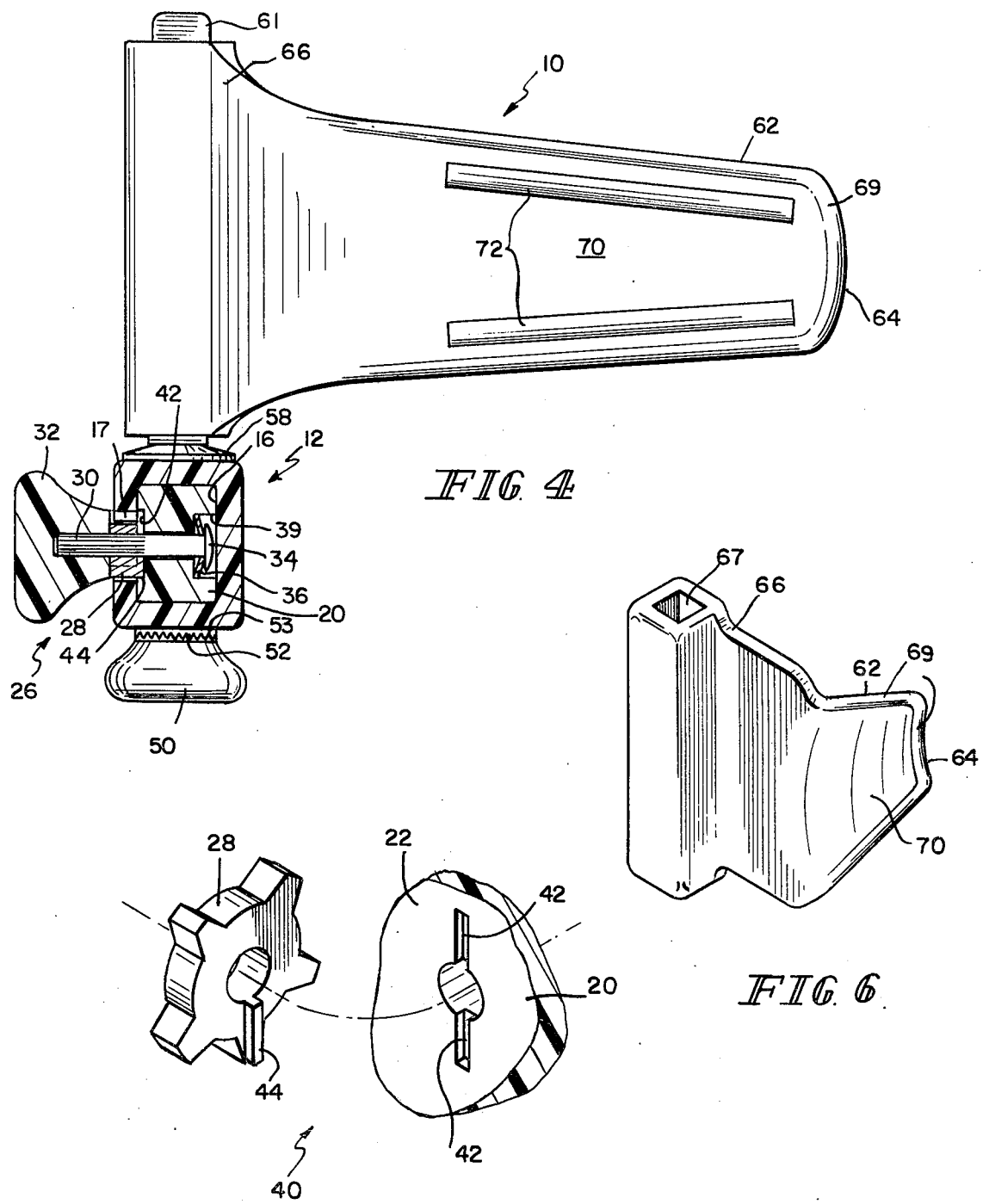
FIG. 4 is a fragmentary cross-sectional view of the apparatus of FIG. 1 taken generally along section lines 4—4 of FIG. 1.
FIG. 5 is an exploded fragmentary perspective view of a detail of the apparatus shown in the cross-sectional view of FIGS. 1–4.
FIG. 6 is a perspective view of a detail of an alternative structure to that illustrated in FIGS. 1–4.

Referring particularly to FIG. 1, a speculum 10 includes a base 12 having first and second members 14 and 20, respectively, adjustably coupled to each other. First member 14 includes a hollow interior 16. A slot 15 is formed in first member 14 as shown, with a series of gear teeth 17 situated along a surface of the slot 15. Second member 20 includes a portion 22 longitudinally movably received within the interior 16 of the first member 14. As illustrated in FIG. 1, a crown gear-like ring 52 has been provided on the underside of each of base members 14, 20. The rings 52 may be attached to the base members 14 and 20 by any suitable means or may be formed with the base members 14 and 20 themselves. The purpose of rings 52 will be explained subsequently.

The base 12 further includes means 26 rotatably coupled to portion 22 of base member 20 for incrementally adjusting the distance between the distal portions 18 and 24 of the base members 14 and 20 respectively. Incremental adjusting means 26 includes a spur gear 28 fixed to a rotatable shaft 30. A knob 32 is attached to shaft 30 for rotation by the speculum operator to rotate gear 28. The spur gear 28 includes a plurality of teeth which engage teeth 17 situated along the surface of slot 15 in base member 14. When the speculum operator rotates the knob 32, the distal portions 18 and 24 of the base members 14 and 20, respectively, are adjusted to a desired separation. The spur gear 28 can be formed separately from, or formed on, the knob 32.

Referring to FIGS. 4 and 5, the incremental adjusting means 26 further includes means 40 for maintaining a desired separation between the distal ends 18 and 24 of the base members 14 and 20. Referring specifically to FIG. 5, means 40 includes a rib 44 situated on the back side of spur gear 28 which engages one of two slots 42 formed in portion 22 of base member 20. By engaging rib 44 in one of slots 42, spur gear 28 is prevented from further rotation until the speculum operator desires to change the distance between the distal portions 18 and 24 of base members 14 and 20.

As illustrated in FIG. 4, a head 34 is provided on the end of shaft 30 opposite knob 32. Head 34 is located in a recess 39 in member 20. Head 34 retains a spring washer 36. The speculum operator disengages rib 44 from a slot 42 by pulling hand grip 32 outward and engages rib 44 in a slot 42 by releasing the hand grip 32. The speculum operator is thus capable of incrementally adjusting the distance between the distal portions 18 and 24 of base members 14 and 20, respectively, and upon adjustment to a desired distance the speculum operator releases the hand grip 32 to sustain the desired distance until further adjustment is desired. Of course, more than one rib 44 and more than two slots 42 could be provided.

Referring again to FIGS. 1 and 2, speculum 10 further includes two elongated shafts 56 which are rotatably mounted in base members 14 and 20 at their distal portions 18 and 24 respectively. As illustrated in FIG. 2, the shafts 56 extend through apertures 21 located in the distal portions 18 and 24 and into the members 50. The members 50 have crown gear teeth 53 provided in their surfaces adjacent the rings 52. Engagement of teeth 53 with respective rings 52 prevents the shafts 56 from rotating in members 14, 20 from selected rotational positions.

If continuous, rather than discrete adjustment of shafts 56 in members 14, 20 is required, alternative means 54 may be provided instead of rings 52 and cooperating teeth 53 to prevent shaft 56 rotation with respect to members 14, 20. The alternative means 54 is provided for each base member 14 and 20 for sustaining a rotational position of shafts 56 once the speculum operator has independently rotated the shafts to desired rotational positions. The alternative means 54 in FIGS. 1 and 2 are thumbscrews threaded into apertures located in the base members 20 and 14. By advancing screws 54, the shafts 56 are engaged, thereby preventing rotational motion until desired by the speculum operator. Means 54 are shown for purposes of illustration only in the embodiment of FIGS. 1,2. Means 54 are not necessary to the proper operation of that embodiment. It will be understood that other known means could be utilized for sustaining rotational positions of shafts 56.

Two members 62 are provided for dilating or enlarging an incision, orifice, or meatus. Each member 62 has a distal end 64 for contacting and restraining a portion of the orifice and a proximal end 66 detachably engaging a portion of the elongated rotatable shaft 56. Each member 62 also includes a shoulder 63 adjacent its proximal end 66. Shoulders 63 rest against external body surfaces to support the speculum 10 away from the external body surfaces and prevent, to the greatest possible extent, contamination of the speculum members 14, 20, 56 by organisms on such external surfaces. The edges 69 of the members 62 are beaded, or rounded, to remove any sharp edges from them and minimize the likelihood of tissue damage from edges 69. The elongated rotatable shafts 56 are engaged in sockets 67 provided on the proximal ends 66 of members 62 to mount the members 62 on the distal portions 18 and 24 of base members 14 and 20, respectively.

Each member 62 is elongated, has a concave inner surface 70, and has disposed on the concave inner surface 70 two elongated ribs 72, each of which includes an aperture 74 extending the length of the rib 72. Light from an external light source (not shown) may be directed along the ribs 72 and down the concave inner surfaces 70 of members 62 directly into the orifice or incision. Since members 62 are detachable from the shafts 56, various other shapes and sizes of members 62, such as is illustrated in FIG. 6, may be used with the speculum 10 depending upon the size, shape, or depth of the orifice, incision or meatus desired to be dilated. Furthermore, members 62 may have at least their distal ends 64 covered with a layer of some material (not shown) which is capable of absorbing body fluids such as blood, and may be removed and either sterilized or disposed of after each use without disposing of the entire speculum 10. Accordingly, members 62 may be fabricated from any desirable material such as metal, plastic, etc. Preferably, members 62 will be constructed from a transparent plastic to permit light transmission through them and to permit an Examiner to view the walls of the orifice or incision through them.

As further illustrated in FIGS. 1 and 2, the portions of rotatable shafts 56 which are engaged by the detachable members 62 includes means 60 on the shafts 56 for preventing members 62 from rotating about shafts 56. Means 60 includes a rectangular portion 61 of each shaft 56. Rectangular portions 61 extend through the sockets 67 in the proximal ends 66 of members 62. Spring washers 58 are interposed between the rectangular portions 61 of shafts 56 and the respective base members 14 and 20 to urge rectangular portions 61 away from members 14, 20 and teeth 53 into engagement with rings 52.

Means 68 are coupled to the proximal ends 66 of members 62 for sustaining desired positions of the members 62 along the shafts 56. The sustaining means 68 include thumbscrews in threaded apertures located in the proximal ends 66 of members 62. By advancing thumbscrews 68, the extended rectangular portion of shaft 56 is engaged, fixing the positions of the members 62 along the shafts 56. It should be noted that members 62 may be independently rotatably adjusted through various angles and sustained at various positions along their respective shafts 56 independently of each other, permitting the speculum operator the flexibility to adjust the speculum 10 to accommodate various types and shapes of orifices.

Having thus described in detail an embodiment of the invention, the operation of speculum 10 will now be described by referring to FIGS. 1, 3 and 4. The speculum operator can make several adjustments to the speculum 10 in order to adapt the speculum 10 to various sizes, shapes, and depths of orifices to be enlarged and/or examined. Means are provided for sustaining the various adjusted positions of the speculum 10 during the examination process, leaving the speculum operator's hands free to perform necessary functions. The speculum operator selects from various shapes and sizes of members 62 the type which is suitable for the orifice to be dilated. The two members 62 may be selected independently and therefore do not necessarily have to be of the same size and shape themselves. Furthermore, as has previously been described, the members 62 may be independently positioned on the shafts 56. Once the speculum operator has selected and attached the desired members 62, the distance between the proximal ends 66 of the members 62 may be incrementally adjusted to permit unobstructed access to the orifice after it is enlarged. This incremental adjustment is accomplished by pulling knob 32 outward and rotating it. As soon as a desired relationship is attained, the speculum operator releases the knob 32, spring washer 36 causing rib 44 to engage one of grooves 42 (FIG. 5) to lock members 14, 20 in a desired relative orientation.

As illustrated by FIG. 3, the distal ends 64 of members 62 may be positioned independently of the positioning of the proximal ends 66 of members 62 by rotating shafts 56. This is achieved by pulling downwardly on knobs 50 against the urging of spring washers 58 (FIGS. 1, 2 and 4) to disenage teeth 53 from rings 52. The knobs 50 are rotated until the shafts 56 reach the desired positions. The knobs 50 are released to permit spring washers 58 to reengage teeth 53 with rings 52. Upon initial entry and contact with the walls of the orifice to be dilated (not shown), the members 62 may be rotated to a position 172 (FIG. 3) wherein the distal ends 64 are in contact with each other, facilitating the initial entry. After entry, the members 62 may be independently rotated by rotating knobs 50, to positions 174 and 76 in which the orifice is enlarged or dilated to a desired width. It is important to note that the initial dilation of the orifice may be accomplished independent of any adjustment of the proximal ends 66 of members 62. In the embodiment utilizing thumbscrews 54 instead of rings 52 and teeth 53, once the desired rotational positions of members 62 have been established, the position of each member 62 may be independently locked by a thumbscrew 54. After the initial dilation of the orifice has been achieved, the distance between the proximal ends 66 of members 62 may be further incrementally increased in order to widen further the dilation or may be incrementally decreased in order to lessen the dilation.

Figure 7:
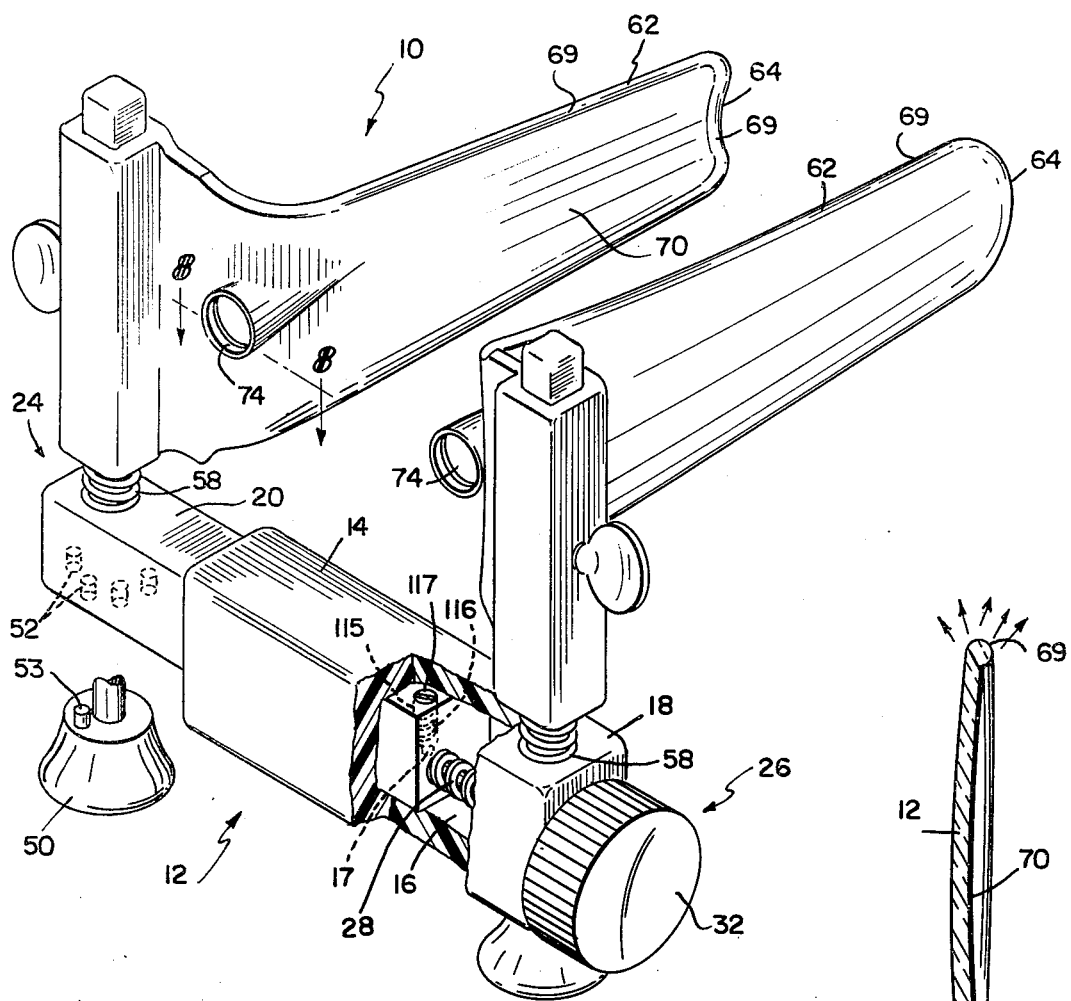
FIG. 7 is a perspective view of another apparatus constructed according to the present invention; and, FIG. 8 is a fragmentary sectional view of the apparatus of FIG. 7, taken generally along section lines 8—8 thereof.
Figure 8:
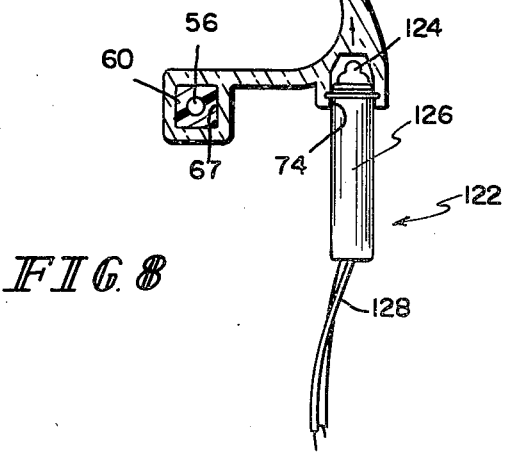

Referring to the embodiment of the invention illustrated in FIGS. 7-8, those components performing the same or similar functions as the corresponding elements in the embodiment of FIGS. 1-6 are numbered similarly.

In FIG. 7, the speculum 10 includes base 12 having first and second members 14 and 20, respectively, adjustably coupled to each other. First member 14 includes hollow interior 16. Second member 20 includes a portion 22 longitudinally movably received within the interior 16 of the first member 14. As illustrated in FIG. 7, a pin 53 is formed on each member 50. A plurality of pockets 52 are provided in each member 14, 20 to receive the pins 53 in each of various selected orientations of the contacting members 62 in this embodiment. The pins 53 are urged upward into engagement with pockets 52 in this embodiment by coil springs 58.

The base 12 further includes means 26 rotatably engaging portion 22 of base member 20 for incrementally adjusting the distance between the distal portions 28 and 24 of the base members 14 and 20, respectively. Incremental adjusting means 26 in this embodiment includes a threaded shaft 28 rotatably engaged in the end 18 of base member 14. Threaded shaft 28 includes a knob 32 rotatable by the speculum operator to rotate shaft 28. The shaft 28 threads engage a bearing 17 which is situated in a bore 115 in the base member 14 and spring loaded into engagement with the troughs in the threads of shaft 28 by a coil spring 116 which is captured between the bearing 17 and a threaded plug 117. When the speculum operator rotates the knob 32, the distal portions 18 and 24 of the base members 14 and 20, respectively, are adjusted to a desired separation. The pitch of the threads on shaft 28 is such that this adjustment will be maintained even under substantial load.

For the purpose of providing light, especially during certain types of surgical procedures, a light source may be coupled to the members 62 through a fiber optic material, such as flexible glass fiber or one of certain types of acrylic resins, such as polymethylmethacrylate. The light source and optical waveguide are constructed as an attachment to a speculum of the type described herein, which may be used as a plastic vaginal speculum or proctoscope, or an abdominal retractor.

In the embodiment of FIGS. 7-8, each contacting member 62 is provided with a socket 74 adjacent its respective shaft 56. Sockets 74 are adapted to receive light sources 122. The light source 122 shown in FIG. 8 includes lamp bulb 124 which extends into the socket 74, a bulb receptacle 126 and wires 128 connecting receptacle 126 to a power source (not shown). The light source could be battery operated. Light from the lamp bulb 124 is guided to the distal end 64 of its respective member 62 by the material from which member 62 itself is constructed. Several suitable materials having optical wave guiding properties are known. Among them is polymethylmethacrylate (LUCITE or PLEXIGLAS). Light from source 122 is directed by the configuration of the material in member 62 down the concave inner surfaces 70 of members 62 directly into the orifice or incision. As with the embodiment of FIGS. 1-6, the operator of the speculum of FIGS. 7 and 8 can make several adjustments to the speculum 10 in order to adapt the speculum 10 to various sizes, shapes, and depths of orifices to be enlarged and/or examined. The speculum operator selects from various shapes and sizes of members 62 the type which is suitable for the orifice to be dilated. The distance between the proximal ends 66 of the members 62 may be adjusted to permit unobstructed access to the orifice after it is enlarged. This adjustment is accomplished by rotating knob 32.

The distal ends 64 of members 62 may be positioned independently of the positioning of the proximal ends 66 of members 62 by pulling knobs 50 downward against the urging of coil springs 58 to pins 53 from pockets 52 and rotating knobs 50. Once desired rotational positions of members 62 have been established, the position of each member 62 may be independently locked by releasing knobs 50 to reengage pins 53 and pockets 52.

The embodiments and methods of operation described hereinabove are not to be construed as excluding other embodiments or modes of operation of the speculum 10.

The construction illustrated, with the base members 14, 20 out of the way, permits easy access to the orifice with surgical instruments and the like.

What is claimed is:

1. A speculum comprising a base including first and second members for movement with respect to one another, means for adjusting the distance between a distal portion of the first member and a distal portion of the second member, the means for adjusting the distance between the distal portions of the first and second members including a pinion gear, means for connecting the adjusting means to the second member, the connecting means including means for selectively rotatably attaching the pinion gear to the second member, and a rack engaging the pinion gear, the rack provided on the first member, first and second shafts, means rotatably supporting each shaft from the distal portion of a respective one of the first and second members, and means for dilating an orifice, the dilating means being provided on the first and second shafts, the dilating means being responsive to adjustment of the first and second members and rotation of the first and second shafts.

2. The apparatus of claim 1 wherein each of said dilating means includes an end portion detachably engaging a respective one of said shafts.

3. The apparatus of claim 2 wherein said detachable engaging means on said dilating means includes sockets for receiving respective shafts, each said shaft and respective socket having a cross-sectional shape for preventing said dilating means from rotating with respect to said elongated shafts, rotation of said shafts causing corresponding rotation of said dilating means about their respective shaft axes.

4. The apparatus of claim 1 including manually adjustable screw-threaded means engageable with said shafts for independently sustaining desired rotational positions of each of said dilating means.

5. The apparatus of claim 1 wherein at least one of said dilating means includes an inner surface along which is disposed at least one lengthwise rib for guiding light into said orifice during use of said speculum.

6. A speculum comprising a base including first and second members for movement with respect to one another, means for adjusting the distance between a distal portion of the first member and a distal portion of the second member, means for connecting the adjusting means to one of the first and second members, first and second shafts, means rotatably supporting each shaft from the distal portion of a respective one of the first and second members, and means for dilating an orifice, the dilating means being provided on the first and second shafts, the dilating means being responsive to adjustment of the first and second members and rotation of the first and second shafts, and means engageable with said shafts for independently sustaining desired rotational positions of said dilating means including a toothed ring provided on at least one of the first and second base members, a passageway through said at least one of the first and second base members for a respective one of said first and second shafts, said at least one passageway extending through its respective toothed ring, a toothed portion fixed to said at least one shaft and spring means for urging the toothed portion on said shaft into engagement with said toothed ring to prevent rotation of said shaft with respect to its respective base member.

7. A speculum comprising a base including a first base member providing an interior and a second base member for movement within said interior, means including a pinion gear for adjusting the distance between a distal portion of said first member and a distal portion of said second member, means for connecting said pinion gear to one of said base members, the connecting means including means for selectively rotatably attaching the pinion gear to said one of said base members, the adjustment means further including a rack provided on the other of said base members for engaging the pinion gear, two shafts, means rotatably coupling each of the shafts to the distal portion of a respective base member, and means for dilating an orifice, the dilating means being provided on said shafts, said dilating means responsive to selective adjustment of said first and second base members and rotation of said elongated shafts selectively to dilate the orifice.

8. A speculum comprising a base including a first base member providing an interior and a second base member for movement within said interior, means for adjusting the distance between a distal portion of said first member and a distal portion of said second member, said means for adjusting said base including a pinion gear, means for connecting said adjusting means to said second base member, said connecting means including means for selectively rotatably coupling said pinion gear to said second base member, said first member including a slot in a wall thereof, the slot extending longitudinally of the direction of movement of the second base member, the slot including a side wall providing a rack for engaging the pinion gear, two shafts, means rotatably coupling each of the shafts to the distal portion of a respective base member, and means for dilating an orifice, the dilating means being provided on said shafts, said dilating means responsive to selective adjustment of said first and second base members and rotation of said elongated shafts selectively to dilate the orifice.

9. The speculum as recited in claim 8 wherein each of said dilating means includes an end portion detachably engaging a respective one of said shafts.

10. The speculum as recited in claim 9 wherein said detachable engaging means on said dilating means includes sockets for receiving respective shafts, each said shaft including means for preventing said dilating means from rotating with respect to said elongated shafts, whereby rotation of said shafts causes corresponding rotation of said dilating means.

11. A speculum including at least two members for dilating an orifice, a shaft for supporting each dilating member, means for connecting each dilating member to a respective shaft, each dilating member having a proximal end engaging a respective shaft and a distal end for insertion into the orifice, a base rotatably supporting at least one of said shafts, the base including a passageway for said at least one shaft, said shaft being rotatably mounted in its passageway, and means for adjusting the distance between the distal ends of the dilating members including first means on the base and second means on said at least one of the shafts engaging the first means in at least selected positions of said at least one of the shafts to prevent rotation of said at least one of the shafts with respect to said base, the first means on the base including a toothed ring on the base surrounding the passageway and a toothed ring on said at least one shaft for engaging a respective toothed ring on the base, and a spring on said at least one shaft for yieldably urging the toothed ring on said at least one shaft into engagement with its ring on the base.

12. The apparatus of claim 11 wherein said dilating member proximal ends detachably engage their respective shafts, said shafts and dilating members cooperatively including means for preventing said dilating member from rotating with respect to said shafts.

13. A speculum comprising a base including first and second members for movement with respect to one another, means for adjusting the distance between a distal portion of the first base member and a distal portion of the second base member, the adjusting means including a pinion gear rotatably mounted on one of the first and second base members and a rack engageable by the pinion gear and provided on the other of the first and second base members, and means for locking the pinion gear against rotation in a selected position to prevent unwanted relative movement between the first and second base members, means for connecting the adjusting means to one of the first and second members, means for dilating an orifice, and first and second means rotatably supporting respective dilating means from the distal portion of a respective one of the first and second members, the dilating means being responsive to adjustment of the first and second base members and rotation of the first and second rotatable support means.

* * * * *